United States Patent [19]

Squirrell

[11] Patent Number: 5,798,214
[45] Date of Patent: *Aug. 25, 1998

[54] CAPTURE ASAYS

[75] Inventor: David James Squirrell, Salisbury, Great Britain

[73] Assignee: The Secretary of State for Defence in Her Britannic Majesty's Government of the United Kingdom of Great Britain and Northern Ireland of Defence Evaluation and Research Agency, United Kingdom

[*] Notice: The term of this patent shall not extend beyond the expiration date of Pat. No. 5,648,232.

[21] Appl. No.: 765,063

[22] PCT Filed: Jul. 12, 1995

[86] PCT No.: PCT/GB95/01643

§ 371 Date: Jan. 6, 1997

§ 102(e) Date: Jan. 6, 1997

[87] PCT Pub. No.: WO96/02666

PCT Pub. Date: Feb. 1, 1996

[30] Foreign Application Priority Data

Jul. 13, 1994 [GB] United Kingdom ............ 9414096

[51] Int. Cl.$^6$ ................ G01N 33/573; G01N 33/569
[52] U.S. Cl. ............ 435/7.4; 435/7.32; 435/15; 435/19; 436/518
[58] Field of Search .................. 435/7.32, 7.4, 435/15, 39; 436/518

[56] References Cited

U.S. PATENT DOCUMENTS

| | | | |
|---|---|---|---|
| 3,933,592 | 1/1976 | Clendenning | 435/8 |
| 4,806,415 | 2/1989 | Fossati | 435/14 |
| 5,648,232 | 7/1997 | Squirrell | 435/34 |

FOREIGN PATENT DOCUMENTS

| | | |
|---|---|---|
| 0217583A1 | 9/1986 | European Pat. Off. |
| 0441469A1 | 1/1991 | European Pat. Off. |
| 0500099A1 | 2/1992 | European Pat. Off. |
| WO94/17202 | 8/1994 | WIPO |

OTHER PUBLICATIONS

Chemical Abstracts, vol. 93, No. 5, issued 1980, Aug. 4, (Columbus, Ohio U.S.A.), S.E. Brolin et al.: "Firefly luciferase assay of adenylate kinase in insulin and glucagon-producing cells" p. 370, No. 40 098j; & Proc.-Int. Symp. Anal. Appl. Biolumin. Chemilumin. 1978 (Pub. 1979), 458–66.

*Primary Examiner*—Michael P. Woodward
*Assistant Examiner*—Donna C. Wortman
*Attorney, Agent, or Firm*—Nixon & Vanderhye

[57] ABSTRACT

A method is provided for determining the presence and/or amount of a microorganism and/or its intracellular material present in a sample performed by: (a) exposing the sample to a specific binding agent that has been immobilized upon a solid substrate, the specific binding agent being capable of binding to the microorganism or its intracellular material such that it becomes associated with the solid substrate, (b) exposing the solid substrate to an agent capable of making adenylate kinase associated with the microorganism and/or its intracellular material accessible to solutions applied to the substrate, (c) applying a solution containing adenosine diphosphate (ADP) to the substrate under conditions whereby adenosine triphosphate (ATP) may be produced by any adenylate kinase present, and (d) measuring the amount of adenosine triphosphate (ATP) and relating that to the presence and/or amount of microorganism or intracellular contents.

22 Claims, 3 Drawing Sheets

CAPTURE ASAYS

CROSS-REFERENCE TO RELATED APPLICATIONS

This application is a 35 USC 371 of PCT/GB95/01643 filed Jul. 12, 1995.

The present invention relates to a method for detecting and assaying microorganisms, to agents for use in such a method, and to test kits comprising essential reagents for carrying out the method.

BACKGROUND OF THE INVENTION

European Patent Application Publication No. 217,583 describes an assay for a ligand extracted from cells, in which the ligand is simultaneously extracted from the cell and reacted with two specific anti-ligands to yield a detectable product.

All living organisms utilise adenosine triphosphate (ATP) as a source of chemical energy and it is known to assay this using the ATP driven luciferase/luciferin reaction. Light generated by this enzymic reaction can be measured using a luminometer and related to the amount of ATP present. The usefulness of ATP as an index of microbial numbers has been known since the mid 1960's (see ATP Luminescence Rapid Methods in Microbiology (1989) editor Stanley et al.; Blackwell Scientific Publications, London, see pages 1–10); its main advantage being speed and sensitivity. Utilising this assay format simple samples can be analysed in a matter of minutes while complex ones samples can be analysed in a matter of minutes while complex ones routinely take only half an hour with a detection capability provided down to $10^{-12}$ mol/l ATP. There is however a need for methods which provide still further sensitivity when detecting microorganisms or their contents while retaining speed and ease of performance.

The present inventor has determined that the speed and sensitivity of ATP based method can be enhanced significantly by shifting the target of the assay from ATP to an enzyme which generates it, particularly to adenylate kinase. Adenylate kinase is an enzyme used by all organisms for the conversion of adenosine diphosphate (ADP) to adenosine triphosphate (ATP). The targeting of this enzyme in preference to ATP, by using the preferred method, reagents and kits of the invention, allows the detection of down to at least $10^{-20}$ moles of intracellular marker adenylate kinase.

It is known to assay adenylate kinase using the luciferase/luciferin system (see Brolin et al Journal of Biochemical and Biophysical Methods 1 (1979) 163–169 and Shutenko et al. Biotekhnologiya, No 4, PA (1988) 542–547) for the purpose of determining its activity and this has been applied to study of certain mammalian and plant tissues (e.g. see Rodionova et al Fiziologiya Rastenii (1978) 25, 4, P731-734). The use of such assay system for the detection and assay of microorganisms however has not been suggested and the advantages of doing such, i.e. enhanced sensitivity so provided, have not been relevant to those studying the enzyme itself.

Although adenylate kinase is present in smaller quantities than ADP or ATP, its use as a biological marker for microorganisms provides enhanced sensitivity with a typical amplification available of 400,000 by measuring its presence through the ATP it produces; that is for every mole of enzyme present 400,000 moles of ADP are converted to ATP in a 10 minute incubation. Thus estimation of the enzyme by measuring the substrate or product of the reaction it catalyses provides for detection down to as low as $10^{-20}$ moles.

The applicant's copending PCT applications PCT/GB94/00118, now U.S. Pat. No. 5,648,232, and PCT/GB94/00766, relate to methods of estimation of microorganisms in a sample from its ability to convert ADP to ATP, and relating that to the presence of microorganisms or their intracellular materials. These applications exemplify methods where magnesium ions, necessary for the reaction of two molecules of ADP with each adenylate kinase active site, are either added as a reagent or provided by any bacteria cells present and as an impurity in the other reagents. The number of cells detected in the examples using such technique proved to be about $10^2$, with results of a more statistically valid nature being obtained at $10^3$ or more; a linear relationship between luminometry counts and cell numbers then being obtainable.

DESCRIPTION OF THE INVENTION

The present invention relates to an improved technique in which adenylate kinase activity is used as a label for microorganisms in a capture assay, wherein once the microorganism has been captured and other reagents removed, that number of microorganisms so captured is determined by making their intracellular contents accessible to ADP, and then measuring the amount of ATP produced, particularly by measuring light produced on performance of the luciferin/luciferase reaction as this provides rapid measurement capability. It will be realised that colorimetric methods for determining the amount of ATP present in a sample may also be used where that is desired, e.g. using pyruvate kinase based reactions; such colorimetric assay linked to the adenylate kinase assay providing excellent sensitivity.

The microorganisms may be captured by any conventional capture assay, e.g. by use of antibodies specific thereto which have been immobilised onto a solid surface, e.g. a microtitre well plate or latex bead. Many alternative surface suitable for immunoassays will occur to those skilled in the art. Particularly preferred in the present method is immobilising the antibodies upon magnetic beads whereupon any microorganisms bound to the antibodies may be captured within a magnetic field, their adenylate kinase activity assessed, and then released such that a further sample of test material may be analysed. Thus in such preferred method continuous flow assay of a sample, e.g. derived from a continuous source such as a cyclone sampler monitoring air bacterial content, may be carried out.

Using the adenylate kinase assay format, particularly with adenylate kinase and ATP depleted reagents, the number of microorganisms present in a sample that can be detected on-line in continuous fashion is of the order of tens per 200 µl sample, and readings with quantitative relation between cells and and ATP derived light are possible down to 10 cells and even fewer than 10 as the reaction volume is reduced.

Thus in a first aspect of the present invention there is provided a method for determining the presence and/or amount of a microorganism and/or its intracellular material present in a sample characterised in that:

(a) the sample is exposed to a capture agent that has been immobilised upon a solid substrate, the capture agent being capable of binding to the microorganism or its intracellular material such that it becomes associated with the solid substrate, (b) exposing the solid substrate to an agent capable of making adenylate kinase associated with the microorganism and/or its intracellular material accessible to solutions applied to the substrate, (c) applying a solution containing adenosine diphosphate (ADP) to the substrate;

(d) measuring the amount of adenosine triphosphate (ATP) produced and relating that to the presence and/or amount of micro-organism or intracellular contents.

The step (d) may be carried out using any of the convenient assays available for assay of ATP. Conveniently these may include a colour forming reaction, but most preferably widely available luciferin/luciferase luminescence reagents are used to detect the conversion of ADP to ATP as will be known by those skilled in the art. The relation of the amount of ATP to the amount of micro-organism and/or intracellular content is readily performed by use of calibration curves prepared by performing the assay method using known amounts of target micro-organism or intracellular material and estimating the unknown amount by comparison with this. For the preferred method a calibration curve of light emitted per number of micro-organisms will be prepared and a reading of light output per unit time from an unknown amount of material in a sample interpreted from that.

In order to maximise the amount of ATP produced, and thus the amplification of the amount of adenylate kinase associated with the solid substrate in the assay the conversion of ADP to ATP is preferably carried out in the presence of magnesium ions at a molar concentration sufficient to allow maximal conversion of ADP to ATP. The amount of magnesium present is preferably such that there is sufficient to provide approximately one mole of magnesium for one mole of ADP such that all of the ADP molecules may be associated with at least one magnesium ion. Note that the reaction is $ADP+Mg^{2+}.ADP \rightleftharpoons Mg^{2+}.ATP+AMP$ therefore a 1:1 ratio is not actually necessary, however it is a useful guide.

In preferred embodiments of this aspect of the invention the sample is provided in the form of an aqueous suspension or solution, any target micro-organisms or materials in the sample captured, and the estimation of adenylate kinase associated therewith is carried out by adding ADP and magnesium ions to the sample under conditions whereby any adenylate kinase present will convert ADP to ATP, the sample incubated for a predetermined period to effect such conversion, luciferase and luciferin agents added, the amount of light emitted from the sample determined and related to presence and amount of adenylate kinase.

The capture step is preferably carried out using immobilised antibodies which are specific to a genus, species or class of micro-organism, but may be binding agents specific to particular materials on the cell walls of many different types of micro-organism, e.g. agents such as lectins. Most conveniently the capture agent will be an antibody and it will be linked to the solid substrate using conventional binding techniques, for example, using covalent coupling or streptavidin/biotin interaction. For example, biotinylation of the specific antibody renders it bindable to streptavidin coated surfaces.

In a preferred method magnetic solid substrate is used, particularly magnetic beads such as those available from Dynal UK Ltd. Station House, 26 Grove Street, New Ferry, Wirral, Merseyside. Methods for binding specific antibodies to these beads will be known to those skilled in the art and discussed in the manufacturer's literature.

Use of such beads allows the target micro-organism to be bound to the bead immobilised antibodies in a solution, including that passing down a conduit such as in a continuous sampling apparatus, to be collected at a treatment station by application of a magnetic field, treated to render adenylate kinase accessible while ADP and ATP measuring assay reagents are supplied. Preferably ADP, magnesium and luciferase/luciferin reagents are added while the beads are immobilised and light emitted is measured using a light detector such as a luminometer adjacent the station. The luciferase/luciferin reagents may be added simultaneously with the ADP and magnesium, or subsequently.

The method of the invention may be performed in a single assay vessel by adding magnetic beads with antibody immobilised thereon to the vessel, adding the sample to be assayed as a solution or suspension and stirring it, immobilising the beads with any captured micro-organisms and/or material using a magnetic field, removing residual solution or suspension, adding ADP substrate and extractant solution or solutions for rendering the adenylate kinase accessible to ADP solution, removing the magnetic field and stirring the beads in the substrate solution, immobilising the beads by reapplication of the magnetic field, removing solution containing the ADP, extractant and any ATP formed and assaying it for ATP. The assay for ATP may be performed by calorimetric assay or, as preferred, luminometry.

A further preferred method using a capture column which comprises binding agent, e.g. antibody, immobilised on solid substrate, e.g. beads, and passes the sample and various reagents down the column sequentially to achieve output of synthesised ATP which is measured and related to presence of the antibody target material.

In all cases, the amount of ADP with which the sample is mixed is preferably sufficient to provide an ADP concentration in the mixture in excess of 0.005 mM, more preferably in excess of 0.01 mM and most preferably in excess of 0.08 mM. A particularly preferred amount of ADP in the conversion step mixture is about 0.1 mM. This may depend upon the purity of the ADP: high levels of contamination with ATP restrict higher concentrations being used. The ranges that would be practically useful for ADP are from approximately 10 mM to approximately 0.1 μm. For the preferred concentrations of ADP set out above, the preferred concentration of magnesium ions in the suspension or solution during conversion of ADP to ATP is 1 mM or more, more preferably 5 mM or more and most preferably 10 mM or more. The magnesium ions may be provided in the form of any magnesium salt, but preferably as magnesium acetate. The ranges that would be practically useful for $Mg^{2-}$ are from approximately 0.1 mM to approximately 25 mM. The amount of $Mg^{2-}$ present may depend, amongst other things, on ADP concentration and amount of chelator (e.g. EDTA) present.

A further preferred format of the present invention adds the luciferin/luciferase luminometry reagents to the sample at the beginning of the incubation, preferably as a single reagent with the ADP and magnesium ion source. This format requires the provision of luciferase reagent of high purity in terms of removal of adenylate kinase during its production. In formats of the invention where all the reagents are included at the start of the conversion of ADP to ATP in this manner, and/or where luminometer counting is continued after luciferin luciferase addition where that is a separate step, magnesium may be provided by the luciferin luciferase reagent. However, due to binding of magnesium ions by luciferase and EDTA it is necessary that the amount of magnesium ions is positively ensured by prior experiment or calculation. It will be realised by those skilled in the art that the optimal amount of magnesium salt to be added to a given ADP, sample and luciferin luciferase mixture will be readily determinable by routine experiment using a sample containing a known amount of bacteria, e.g., *E. coli*, whereby maximal signals are obtained.

As magnesium ions can cause instability in ADP (in terms of allowing contaminating adenylate kinase to prematurely convert it to ATP) it is preferred not to keep them in solution together prior to use, preferably they are brought together just prior to use or in the ADP conversion step. As magnesium ions are required for the activity of adenylate kinase it may be preferred to mix these and the sample together before adding ADP. Where the reagents are to be kept together it is preferred that they are kept in freeze dried form to avoid any unstabilising effects.

As stated above, adenosine triphosphate (ATP) is preferably detected by use of the luciferin luciferase system to provide a photometrically detectable signal indicative of the amount of ATP in the sample. Luciferin/luciferase preparations and methods for their use in assaying ATP will be well known to those skilled in the art and are commercially available (e.g. see Brolin et al). A typical formulation contains e.g. 0.1 to 10 mg/liter luciferase, 15 to 1000 μmol/liter, preferably 15 to 100 μmol/liter (e.g. ~36 μmol/liter) D-luciferin, and agents such as $MgCl_2$ (2.5–25 mmole) EDTA, BSA, and pH7 buffer (see e.g. EP 054676) more typically pH7.8.

For single reagent use with adenylate kinase testing methods as described herein it is preferred that the pH is adjusted to that which is optimal for both enzymes, i.e. a compromise, in order that counting might continue while converting ADP to ATP. This may be determined by routine experiment using known bacterial numbers in a sample. The sample, ADP and magnesium ion source may be mixed in any buffer providing a pH suitable for the adenylate kinase reaction; no other reagents are necessary. Thus any buffer providing a pH of between 5.5 and 8.5 might be used, with optimal pH lying between pH6 and 7, preferably pH6.5. Examples of suitable buffers include Tris and phosphate buffers. Most suitably the sample is collected and/or diluted in such a buffer in preparation for carrying out the method of the invention.

As with any amplified assay, the sensitivity of the adenylate kinase assay of the present invention is limited by the purity of the reagents. In this case the significant contaminants are ATP in the ADP substrate and adenylate kinase in the luciferase preparation. For use as a sensitive assay for micro-organisms, particularly where these may be potentially harmful and need detecting in low numbers, it is necessary that the purity of each of the reagents be as high as possible with respect to the substance with which it is to react in the assay.

Using a preferred Econopaq Q strong anion exchange gel cartridge (BioRad) equilibrated with 20 mM potassium phosphate at pH4.6 and eluting with steps of KP (potassium phosphate) concentration up to 400 mM, ADP was found to be eluted as a coherent peak with ATP eluting after it. In this manner ADP with a molar % ATP upper limit of $2 \times 10^{-8}$ was obtainable. The most pure ADP the applicants are aware of from the literature is 0.001% (see Shutenko et al. as above) thus the present invention provides ADP for use in the method of the present invention that has less than 0.001 molar % ATP, more preferably $2 \times 10^{-8}$ molar % or less.

With regard to the second problem, adenylate kinase, as an essential "housekeeping" enzyme, is present in virtually all organisms and is generally present in luciferase preparations. It may only be a minor contaminant, but since the aim is to measure very low adenylate kinase levels in samples, its presence in the luciferase may be a limiting factor.

The molecular weights of luciferase and adenylate kinase are significantly different, being 61 kD and 21 kD respectively. Furthermore luciferase is a membrane associated protein and therefore relatively hydrophobic, whereas adenylate kinase occurs as a soluble enzyme. It is thus possible to remove adenylate kinase from luciferase preparations by, e.g. size exclusion chromatography, reverse phase chromatography, or both. Alternatively or in addition to this, the problem of adenylate kinase contamination of luciferase can be avoided by adding the bioluminescent reagents (luciferase and luciferin) just before or as measurements are taken so that any contaminating adenylate kinase does not have the time to produce a significant effect.

Suitable methods for purifying luciferase use column chromatography fractionation with a low porosity gel, e.g. Sephadex G-25 (see Nielsen and Rasmussen, Acta Chemica Scandinavica 22 (1968) p1757–1762; use of Sephadex and Sepharose columns (e.g. Blue Sepharose) in series and by SDS electrophoresis (see Devine et al. Biochimica et Biophysica Acta 1172 (1993) 121–132) or aging for a period at elevated ambient temperature.

A source of adenylate kinase free BSA, a component of commercial luciferase/luciferin preparations, is the chemically treated reagent acetylated-BSA, available from Sigma and BDH. It will be realised by those skilled in the art that other chemically treated BSAs will also be suitable.

In order to render all the adenylate kinase associated with a target micro-organism available to the ADP, magnesium ions and luciferase/luciferin assay reagents of the invention it will be necessary to disrupt them such that intracellular material is released or otherwise exposed to the agents. Such disruption might be carried out using mechanical means such as an ultrasonic generator, by use of osmotic shock optionally in association with cold shock or such agents as lysozyme or, more conveneniently, by use of detergents. Such detergents are commercially available and commonly referred to as 'extractants'. Typical extractants include generic cationic detergents such as CTAB (Cetyl Trimethyl Ammonium Bromide), and proprietary agents such as Enzymatics ATP releasing agent, Biotrace XM extractant (available from Biotrace, Bridgend UK), Celsis UK cationic extractants and Lumac NRM (nucleotide releasing agent available from Lumac BV, Holland). When using CTAB a convenient preparation will include 0.01 to 1% CTAB in water, e.g. 0.2%, but other concentrations may occur to those skilled in the art.

Thus before adding ADP and luciferase/luciferin reagent (s) to an assay sample suspected of containing micro-organisms it is preferred to disrupt these to render their intracellular contents accessible to luminometry reagents by use of disrupting agent. If it is desired to distinguish between target cells and cells such as those of fungal spores it is possible to run two separate assays treating one with a nonionic detergent capable of disrupting only those spore and multi-cellular 'somatic' animal cells (e.g. Triton X-100 available from Sigma) and the other with cationic detergent 'extractants' detailed above for disrupting all cells. It is possible to carry out these assays on the same sample if an ATPase such as apyrase followed by a protease is added between detergent/luciferase/measurement cycles; one cycle using nonionic and other cationic detergent in a first cycle step.

The effect of extractant upon the luciferase/luciferin system is known to be important (see e.g. Simpson et al (1991) J Biolumin Chemilumin 6(2) pp97–106: with cationic detergents being known to potentiate the reaction but to cause gradual inactivation of luciferase, anionic detergent inhibiting the reaction and nonionic and zwitterionic detergents being known to potentiate over a wide range. A mixture of 0.15% cationic detergent together with 0.25% tertiary diamine surfactant (obtained from Celsis, Cambridge, UK)

was found to be satisfactory for present purposes, but those skilled in the art will have no problem screening for other 'extractants' that yield an optimal mix of adenylate kinase and luciferase activity when copresent in the same solution. Typically a range of detergent concentrations of approximately 0.05% to 1.0% may be used.

The light given off from the mixture after all the essential steps are complete, i.e. ADP conversion to ATP and subsequent action of luciferase upon luciferin, may be measured by residence of the sample volume, e.g. luminometer tube, within a light detector immediately after or simultaneously with addition of the luciferase and luciferin or other agents which enable the essential steps to proceed.

In a second aspect of the present invention there is provided a test kit comprising the essential reagents required for the method of the invention, i.e. immobilised capture agent, adenosine diphosphate and preferably a source of magnesium ions and preferably luciferase and luciferin. Preferably the kit includes all these reagents, with the luciferase and luciferin being provided as a single reagent solution, with a detergent reagent in the kit suitable for disrupting the target cells for which the assay is intended. Usually for assaying micro-organisms only cationic detergent is needed, whereas if fungal spores and somatic cells are likely to be significant then a further nonionic detergent reagent might be included to assess their numbers. The kit is in the form of a single package preferably including instructions as to how to perform the method of the invention; the reagents being provided in containers and being of strength suitable for direct use or after dilution.

A preferred test kit of the invention comprises immobilised antibody, in the form of loose beads, a column filled with beads or a coated microtitre well. ADP reagent which is of purity higher than 99.999%, and a luciferase/luciferin reagent, including BSA, that is substantially free of adenylate kinase activity. Alternatively the luciferase/luciferin ratio used, reflected in the kit instructions for use and/or in their relative concentrations, is such that the luciferase is capable of acting upon the luciferin substrate sufficiently quickly such that any luciferase associated adenylate kinase produces ATP after the initial emission is finished; thus micro-organism derived adenylate kinase will be indicated by a flash kinetic reaction and contaminant ATP by a glow.

Further provided by the present invention is apparatus for performance of the method of the invention comprising a reaction chamber in which the immobilised capture agent is interacted with sample in use, this chamber having inlet and outlet means for supply of reagents in sequential fashion such as to carry out the binding, extractant and ADP addition steps of the assay of the invention, and being connected with a source of luciferase/luciferin reagent to a luminometer flow cell such that on completion of all of these steps, generated ATP can be directly measured by correlation with the amount of light emitted. Preferred reaction chambers of the apparatus of the present invention include:

(a) A reaction vessel located within the range of an electrically operable magnet such that magnetic beads suspended in the vessel in a reaction liquid can be immobilised as required for change of reagents, e.g. under influence of pump means, or (b) a reactor column comprising conventional capture agent support material, e.g. latex beads, coated with capture agent.

The methods, apparatus, reagents and kits of the present invention will now be illustrated by way of example only with reference to the following non-limiting Examples and Figures. Further embodiments will occur to those skilled in the art in the light of these.

EXAMPLE 1

Figure 1:
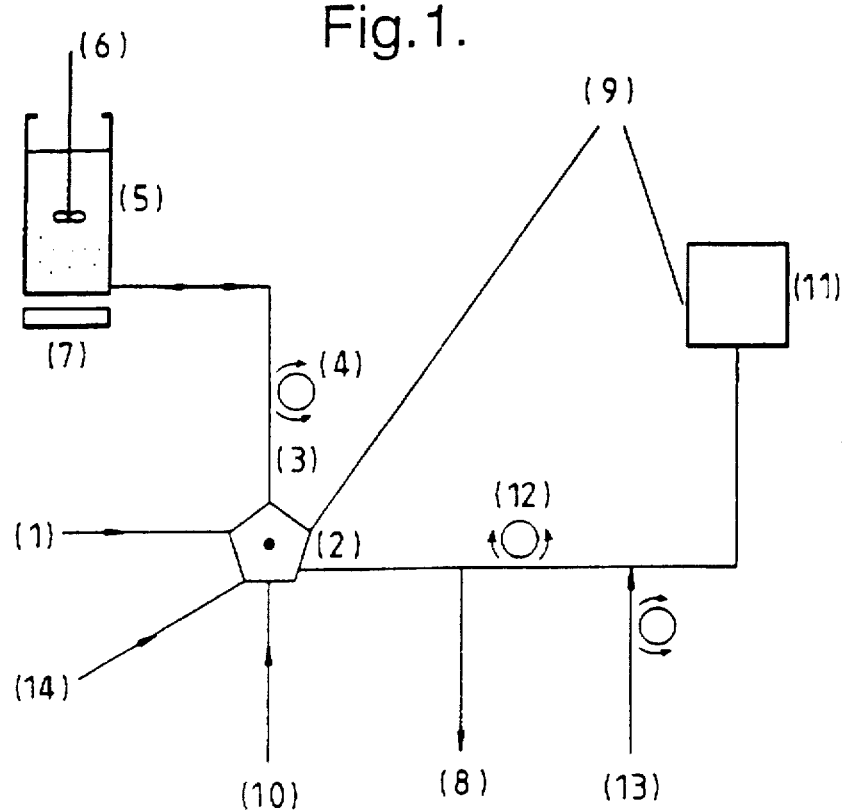
FIG. 1: Shows a diagrammatic representation of an apparatus for performance of the method of the invention using an automated flow system with immobilisation of capture agent on magnetic beads and using a selectively magnetised magnet to trap them.

Assay of *E. coli* Using Apparatus of FIG. 1

A liquid sample containing *E. coli* for assay is supplied from a sample source (1) via a five-way valve (2), peristaltic tubing (3) and reversible pump (4) to a reaction vessel (5) containing antibodies specific to *E. coli* that have been immobilised upon Dynal magnetic beads by conventional covalent coupling. The beads and sample are stirred together for a capture period, e.g. 1 to 30 minutes, using stirrer (6), magnet (7) energised to immobilise the beads, and sample liquid removed to waste (8) via the reversible pump (4) and valve (2). The beads are washed by supply of wash buffer from source (9), deenergisation of magnet (7), operation of stirrer (6), energisation of magnet (7) and removal of buffer to waste.

ADP substrate (>99.999% pure with respect to ATP), magnesium acetate and extractant reagent (0.15% cationic detergent and 0.25% tertiary diamine per final volume) is supplied from source (10) in sufficient quantity to provide 0.1 mM ADP and 10 mM magnesium ions in the reaction vessel, the magnet deenergised and stirrer operated and extraction/ADP conversion allowed to proceed for a set period between of 1 or 5 minutes before the stirrer is stopped, the magnet energised and the liquid removed to the luminometer flow cell (11) using the peristaltic tubing (3) and reversible pumps (4) and (12) while simultaneously mixing it with an effective volume of luciferase/luciferin reagent of depleted adenylate kinase content from source (13). Using an adenylate kinase modified Celsis LDR reagent of otherwise standard amounts of active ingredients this volume is about one half of the volume of the sample. Light emitted in the flow cell is related to the amount of *E. coli* captured by reference to standard curves obtained by performance of the assay with known numbers of cells.

Regeneration of the reaction vessel magnetic beads is carried out by pumping used beads to waste and supplying new ones from source (14), or using a reagent or solution which dissociates the sample from the beads so that the beads are regenerated; for example, if the regeneration is from antibodies then ~0.1M HCl may be used.

EXAMPLE 2

Figure 2:
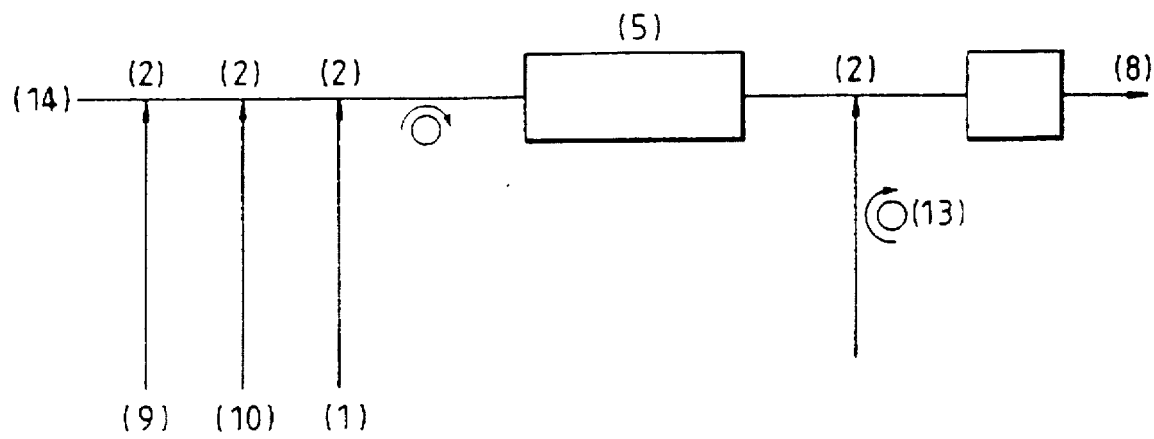
FIG. 2: Shows a diagrammatic representation of an apparatus for performance of the method of the invention using an automated flow system with immobilisation of capture agent on a reactor column.
Figure 3:
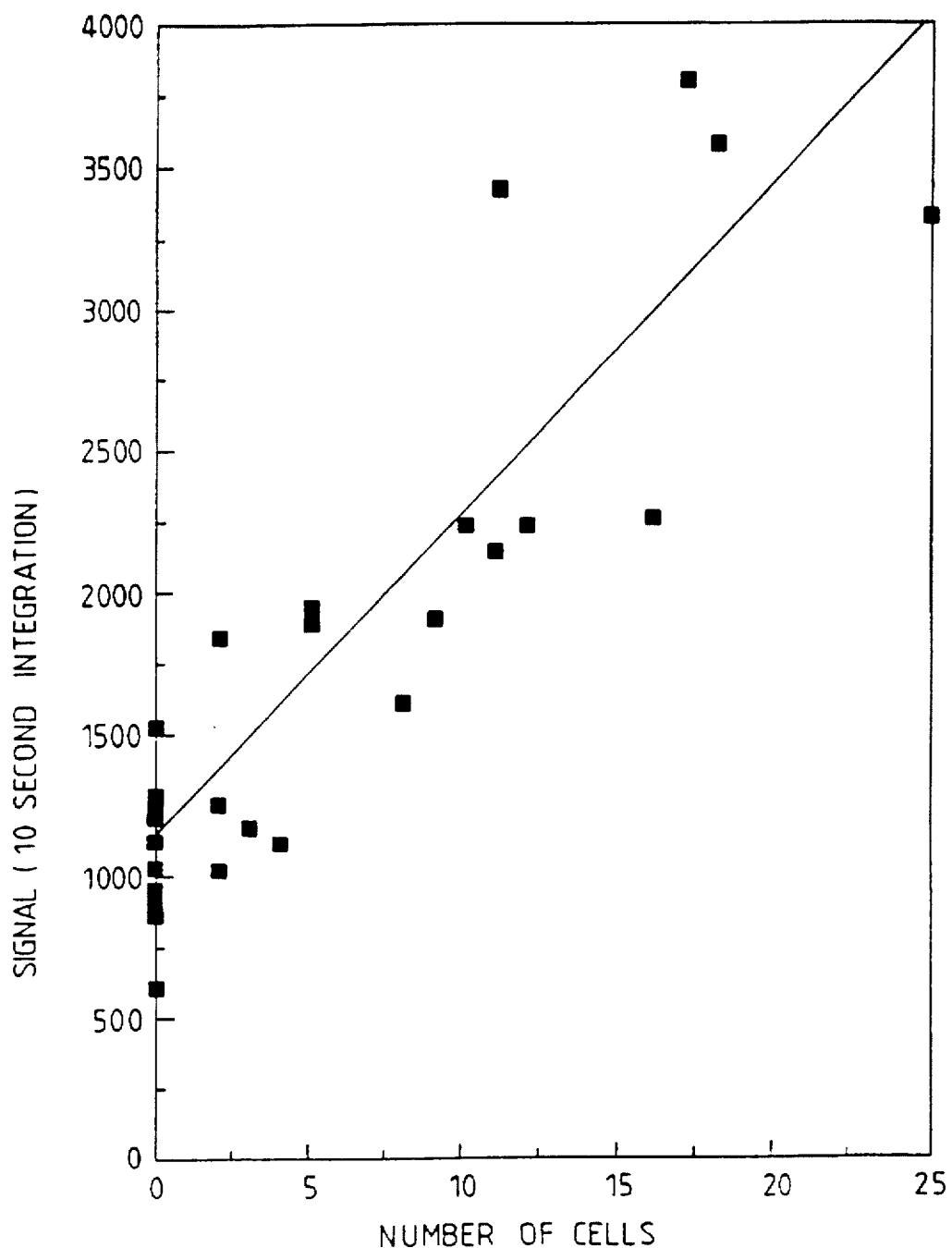
FIG. 3: Illustrates in graphical form Adenylate Kinase Assays for low numbers of *E. coli* cells
Figure 4:
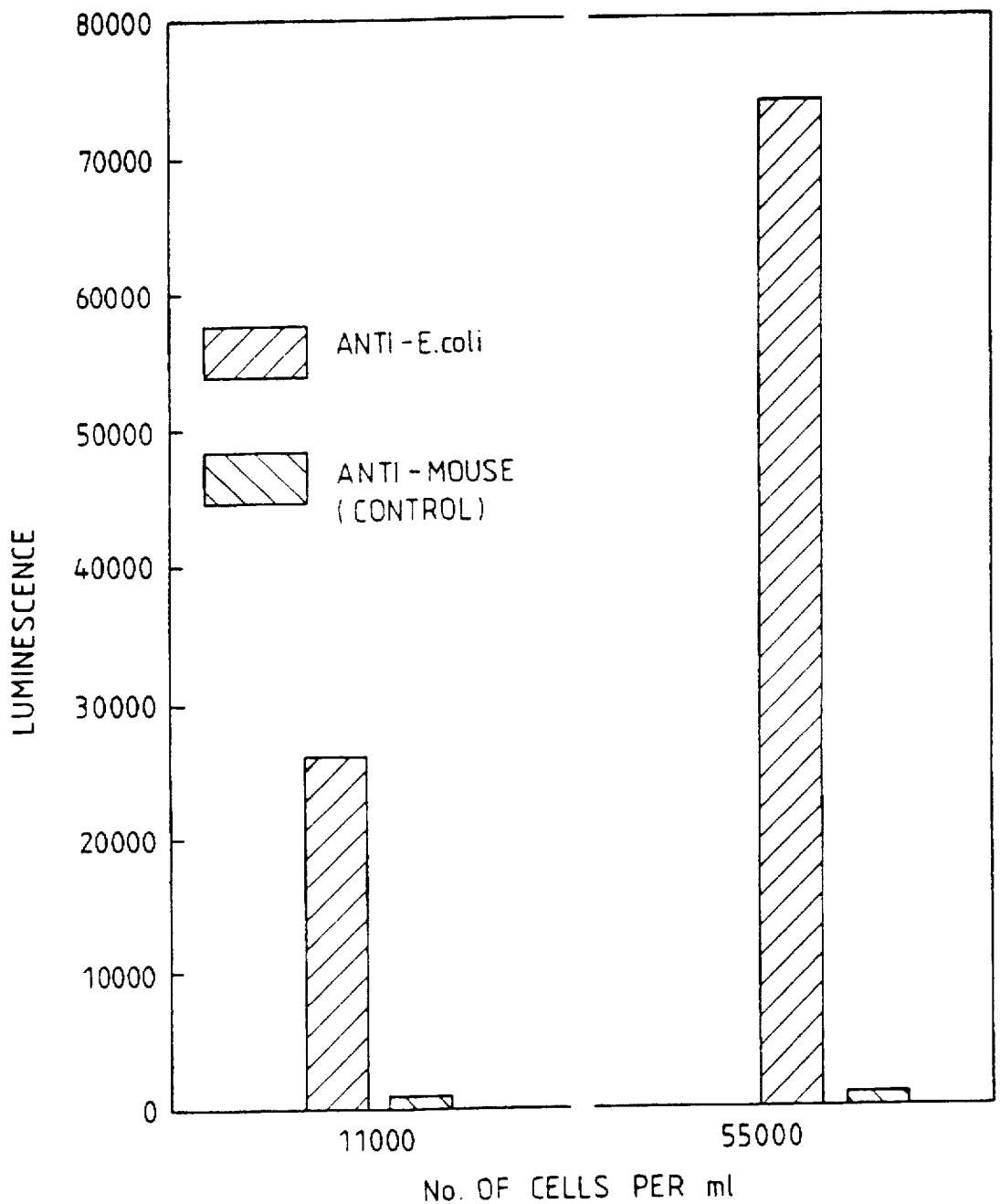
FIG. 4: Illustrates in bar chart form Specific Assay for *E. coli* using magnetic beads for capture and adenylate kinase for detection.

Assay of *E. coli* Using Apparatus of FIG. 2

Assay is performed as per Example 1 but with the vessel (5), magnet (7) and stirrer (6) replaced by a reactor column in-line with a luminometer flow cell and supplied with the reagents from sources annotated as before. Use is made of three two way valves (2) rather than a single five way valve and the pumps are not reversible. The source of sample is derived directly from a hydrocyclone as described in copending UK patent application GB9405392.3.

It will be realised that a five way valve arrangement of Example 1 may be used with such reactor column method, and that the in-line three two way valves may be used with the reaction vessel and stirrer of Example 2. Similarly the assay steps may readily be carried out by manual operation of the magnet and manual addition of reagents.

I claim:

1. A method for determining the presence and/or amount of a microorganism and/or intracellular material present in a sample comprising the steps of:
   (a) exposing the sample to a capture agent that has been immobilised upon a solid substrate, the capture agent being capable of binding to the microorganism or intracellular material such that the microorganism becomes associated with the solid substrate,
   (b) exposing the solid substrate to an agent capable of making adenylate kinase associated with the microorganism and/or its intracellular material accessible to solutions applied to the substrate,
   (c) applying a solution containing adenosine diphosphate (ADP) to the substrate under conditions whereby adenosine triphosphate (ATP) may be produced by any adenylate kinase present
   (d) measuring the amount of adenosine triphosphate (ATP) produced and relating that to the presence and/or amount of micro-organism or intracellular material.

2. A method as claimed in claim 1 wherein step (d) is carried out using an assay that includes a colour forming reaction.

3. A method as claimed in claim 1 wherein step (d) is carried out by use of luciferase/luciferin reagent to produce light proportional to the amount of ATP produced, and said light is detected using a luminometer.

4. A method as claimed in claim 1, wherein the conditions used in step (c) include presence of magnesium ions at a molar concentration sufficient to allow maximal conversion of ADP to ATP.

5. A method as claimed in claim 4 wherein steps (b) and (c) are carried out together by adding extractant, ADP and magnesium ions to the sample and incubating the mixture for a predetermined period to effect conversion of ADP to ATP.

6. A method as claimed in claim 1 wherein the capture agent used in step (a) comprises immobilised antibodies which are specific to a genus, species or class of microorganism or a binding agent specific to particular materials on the cell walls of many different types of micro-organism.

7. A method as claimed in claim 6 wherein the capture agent is an antibody linked to the solid substrate using covalent coupling or streptavidin/biotin interaction.

8. A method as claimed in claim 1 wherein the solid substrate is capable of being held by a magnetic field.

9. A method as claimed in claim 8 wherein step (a) is carried out by adding magnetic beads with antibody immobilised thereon to a vessel, adding the sample to be assayed as a solution or suspension and stirring it, immobilising the beads with any captured microorganisms and/or material using a magnetic field, removing residual solution or suspension, adding ADP substrate and extractant solution or solutions for rendering the adenylate kinase accessible to ADP solution, removing the magnetic field and stirring the beads in the solution, immobilising the beads by reapplication of the magnetic field, removing solution containing the ADP, extractant and any ATP formed, and assaying the said solution for ATP.

10. A method as claimed in claim 1 wherein the capture agent is retained within a column.

11. A method as claimed in claim 10 wherein the capture agent is retained on beads held within the column.

12. A method as claimed in claim 11 wherein the sample and the assay reagents are passed down the column sequentially to achieve output of synthesised ATP which is measured and related to presence of the capture agent target material.

13. A method as claimed in claim 1 wherein the amount of ADP to which the bound sample is exposed is sufficient to provide an ADP concentration of in excess of 0.005 mM.

14. A method as claimed in claim 13 wherein the amount of ADP is sufficient to provide an ADP concentration of about 0.1 mM.

15. A method as claimed in claim 13 wherein the concentration of magnesium ions to which the bound sample is exposed is 1 mM or more.

16. A method as claimed in claim 15 wherein the magnesium ion concentration is 10 mM or more.

17. A method as claimed in claim 1 wherein the step (b) is carried out by adding a reagent comprising a cationic detergent.

18. A method as claimed in claim 17 wherein the reagent comprises a tertiary diamine.

19. A test kit for performing a method as claimed in claim 1, the kit comprising a solid substrate, a capture agent which has been immobilized on said solid substrate and which is capable of binding a micro-organism or intracellular material, and adenosine diphosphate.

20. A test kit as claimed in claim 19 further comprising a source of magnesium ions and/or luciferase and luciferin.

21. A test kit as claimed in claim 20 wherein said capture agent is an antibody immobilised upon a solid support provided in the form of loose beads, a column filled with beads or a coated microtitre well; wherein said adenosine diphosphate is of purity higher than 99.999%; and comprising a luciferase/luciferin reagent including bovine serum albumin (BSA) that is substantially free of adenylate kinase activity.

22. A test kit according to claim 19 wherein the capture agent is an antibody which is specific to a genus, species or class of micro-organism, or is an agent which is specific to particular materials on cell walls of microorganisms.

* * * * *